US012280057B2

(12) United States Patent
Moyer et al.

(10) Patent No.: US 12,280,057 B2
(45) Date of Patent: Apr. 22, 2025

(54) VASOACTIVE TOPICAL COMPOUND TO AFFECT TISSUE BLOOD FLOW, REDUCE TISSUE NECROSIS AND PROMOTE HEALING

(71) Applicant: SOUTH DAKOTA BOARD OF REGENTS, Pierre, SD (US)

(72) Inventors: Hunter Moyer, Rapid City, SD (US); Daniel Heglund, Rapid City, SD (US)

(73) Assignee: SOUTH DAKOTA BOARD OF REGENTS, Pierre, SD (US)

( * ) Notice: Subject to any disclaimer, the term of this patent is extended or adjusted under 35 U.S.C. 154(b) by 150 days.

(21) Appl. No.: 17/447,101

(22) Filed: Sep. 8, 2021

(65) Prior Publication Data

US 2021/0393639 A1 Dec. 23, 2021

Related U.S. Application Data

(63) Continuation of application No. PCT/US2020/021697, filed on Mar. 9, 2020.

(60) Provisional application No. 62/815,616, filed on Mar. 8, 2019.

(51) Int. Cl.
| | |
|---|---|
| *A61K 31/522* | (2006.01) |
| *A61K 31/21* | (2006.01) |
| *A61K 31/5415* | (2006.01) |
| *A61K 31/655* | (2006.01) |
| *A61K 33/06* | (2006.01) |
| *A61K 47/44* | (2017.01) |
| *A61P 7/08* | (2006.01) |
| *A61P 9/08* | (2006.01) |

(52) U.S. Cl.
CPC ........ *A61K 31/522* (2013.01); *A61K 31/5415* (2013.01); *A61K 31/655* (2013.01); *A61K 33/06* (2013.01); *A61K 47/44* (2013.01); *A61P 7/08* (2018.01)

(58) Field of Classification Search
None
See application file for complete search history.

(56) References Cited

U.S. PATENT DOCUMENTS

| | | | | |
|---|---|---|---|---|
| 4,482,534 A | * | 11/1984 | Blank | A61P 9/10 514/742 |
| 4,599,340 A | * | 7/1986 | Silver | A61K 31/44 514/277 |
| 5,919,474 A | | 7/1999 | Place et al. | |
| 8,236,313 B2 | | 8/2012 | Isenberg et al. | |
| 2002/0049188 A1 | * | 4/2002 | Azarnoff | A61K 9/0031 514/509 |
| 2006/0153931 A1 | * | 7/2006 | Stamler | A61K 31/095 424/617 |
| 2010/0051025 A1 | | 3/2010 | Zapol et al. | |
| 2014/0005137 A1 | | 1/2014 | Dobson | |
| 2014/0276493 A1 | | 9/2014 | Leung et al. | |

FOREIGN PATENT DOCUMENTS

| | | | | | |
|---|---|---|---|---|---|
| EP | | 189861 A | * | 8/1986 | ............. A61K 47/10 |
| WO | WO-2005070433 A1 | | * | 8/2005 | ........... A61K 31/522 |

OTHER PUBLICATIONS

Sagi, A., et al. "Prophylactic use of chlorpromazine to improve survival of random skin flaps in pigs." European Journal of Plastic Surgery 20 (1997): 80-83. (Year: 1997).*
Karacaoglan, Naci, and Hayati Akbas. "Effect of parenteral pentoxifylline and topical nitroglycerin on skin flap survival." Otolaryngology—Head and Neck Surgery 120.2 (1999): 272-274. (Year: 1999).*
Lambert, WJ. "Petrolatum." Handbook of Pharmaceutical Excipients. 6th Edition (2009) 481-484. (Year: 2009).*
Cao, Bin, et al. "Effects of lidocaine on random skin flap survival in rats." Dermatologic Surgery 41.1 (2015): 53-58. (Year: 2015).*
Alsaab et al., "Organogels in Drug Delivery: A Special Emphasis on Pluronic Lecithin Organogels", J Pharm Pharm Sci, vol. 19, No. 2, pp. 252-273, 2016.
International Searching Authority in connection with PCT/US2020/021697 filed Mar. 9, 2020, "The International Search Report and the Written Opinion of the International Searching Authority, or the Declaration", 13 pages, mailed May 15, 2020.
Liang et al., "Nitric oxide generating/releasing materials", Future Science OA, vol. 1, No. 1, FSO54, pp. 1-10, 2015.
Pathan et al., "Chemical Penetration Enhancers for Transdermal Drug Delivery Systems", Tropical Journal of Pharmaceutical Research, vol. 8, No. 2, pp. 173-179, Apr. 2009.
Som et al., "Status of surfactants as penetration enhancers in transdermal drug delivery", J Pharm Bioallied Sci., vol. 4, No. 1, pp. 1-15, 2012.
Sood et al., "Comprehensive Invited Review: Wound Dressings and Comparative Effectiveness Data", Advances in Wound Care, vol. 3, No. 8, pp. 511-529, 2014.

* cited by examiner

*Primary Examiner* — Bethany P Barham
*Assistant Examiner* — Peter Anthopolos
(74) *Attorney, Agent, or Firm* — McKee, Voorhees & Sease, PLC

(57) ABSTRACT

The present disclosure relates to compositions and systems for improving tissue perfusion such that blood flow is increased, improving tissue healing time and reducing or eliminating tissue necrosis. In a preferred embodiment, the compositions comprise a phosphodiesterase inhibitor, a calcium channel blocker, a nitric oxide producer, and an α-adrenergic antagonist. Methods of making the compositions and using the compositions are also disclosed.

20 Claims, 3 Drawing Sheets

VASOACTIVE TOPICAL COMPOUND TO AFFECT TISSUE BLOOD FLOW, REDUCE TISSUE NECROSIS AND PROMOTE HEALING

CROSS-REFERENCE

This application is a Continuation Application of PCT/US2020/21697, filed Mar. 9, 2020, which claims priority under 35 U.S.C. § 119 to provisional application U.S. Ser. No. 62/815,616, filed Mar. 8, 2019; each of the foregoing applications are hereby incorporated by reference in their entirety, including, without limitation, the specification, appendices, figures, tables, Examples, and the claims.

TECHNICAL FIELD

The present invention relates to compositions, systems, and methods of use thereof for improving tissue perfusion such that tissue blood flow is increased, leading to the reduction and/or elimination of tissue necrosis. The present invention further relates to methods and systems of promoting tissue healing.

BACKGROUND

Adequate tissue perfusion is key for tissue survival, healing, and function. Severe tissue hypoxia combines with lactic acid produced by bacteria to lower tissue pH, contributing to tissue necrosis. As such, wounds (both traumatic and surgical) in hypoxic tissues are more easily infected and heal extremely slow as epithelial, fibroblast, and leukocyte proliferation is suppressed by low oxygen availability. Wound tensile strength is also limited in the absence of oxygen, increasing the risk of secondary tissue trauma. Thus, the sufficiency of tissue healing depends highly on tissue perfusion.

Inadequate tissue perfusion during and after surgery is a key culprit of a myriad of surgical complications such as colonic anastomotic leaks, peri-prosthetic joint infection, mastectomy reconstruction failures, and vascular graft infections to name a few. Breast reconstruction is one example of surgeries where blood flow is of paramount importance to the outcome. Of the more than 100,000 breast reconstruction procedures performed in the United States every year, approximately 5-30% result in necrosis of the mastectomy skin due to poor blood flow. The estimated cost of this complication is between $13,000 and $40,000 USD per patient.

Problems with tissue perfusion can also occur after injury, trauma and burns. In particular, many individuals with chronic wounds may be unaware of circulation issues and may fail to seek medical assistance until necrosis, ulcers, and other related complications have occurred. With respect to traumatic injuries, adequate tissue perfusion can minimize the occurrence of septic shock and can aid in the speed of recovery. Burn injuries to the skin create a zone of necrosis at the contact site and an area of stasis immediately adjacent to the site. The depth of the burn partly depends on the health of the surrounding zone of stasis, and improved blood flow to this zone can prevent superficial burns from developing into full-thickness burns.

Various co-morbidities often arise together with blood flow disruptions due to surgery, traumatic injury, and chronic wounds. In such cases, tissue perfusion can be further limited due to conditions such as diabetes mellitus, obesity, hypertension, vasculitis, venous stasis, arteriosclerosis, radiation damage, chronic infection, and/or age, among others. These conditions further complicate tissue recovery and healing.

Without adequate tissue perfusion, individuals with chronic wounds and individuals recovering from surgery or traumatic injuries can experience significant consequences such as loss of function, amputation of the affected tissue, and/or death.

Advances in surgical technique are touted to limit these complications, however such advances have not eliminated problems stemming from inadequate circulation. One solution to prevent tissue necrosis in breast reconstruction is the use of tissue expanders. Tissue expanders are temporary implants which stretch the tissue after a mastectomy to prepare for breast reconstruction. Expanders are used as a way to prevent mastectomy flap necrosis; however, tissue expanders necessitate additional surgeries, physician and patient time, and add a new complication profile. Further, the added cost of a tissue expansion phase is at a minimum approximately $7,000 USD per patient.

Another newer solution to the problem of inadequate circulation is to apply a topical nitroglycerin medication to the skin in the immediate post-operative period after mastectomy. The use of nitroglycerin with a single intra-operative application has shown a reduction in mastectomy flap skin necrosis. Although not considered the standard of care yet, a rising number of surgeons are now adopting this technique. Unfortunately, nitroglycerin ointment has many disadvantages. Severe headaches and systemic hypotension can result in the post-anesthesia care unit. The half-life of this medication is on the order of 2 to 5 minutes, thus multiple applications are potentially needed to gain maximum benefit.

Finally, the nitroglycerin product is not supplied sterile and once opened has decontaminated the entire surgical field. In order to maintain surgical field contamination, a product should ideally have a sterility assurance level (SAL) of at least $10^{-3}$ SAL, and preferably at least $10^{-6}$ SAL. More specifically, as $10^{-6}$ SAL is the standard for products intended to come into contact with breached skin, it is preferable that topical applications and wound dressings can provide an assurance of at least $10^{-6}$ SAL.

Additionally, existing topical compositions typical only increase dermal blood flow by acting primarily on veins. It is an object of the present application to provide a composition that increases dermal blood flow by acting on arteries, arterioles, capillaries, venules, veins and the rheologic property of blood.

It is therefore an object of the present application to provide a cost-effective method of improving tissue perfusion in order to minimize and/or prevent tissue necrosis.

It is a further object of the present application to provide a method of improving tissue perfusion which has an improved half-life.

It is also an object of the present application to provide a method of improving tissue perfusion and preventing necrosis which provides an SAL of at least $10^{-3}$ SAL and preferably at least $10^{-6}$ SAL.

Other objects, advantages and features of the present invention will become apparent from the following specification taken in conjunction with the accompanying drawings.

BRIEF SUMMARY

In an embodiment, the present application provides compositions, systems, and methods of improving tissue perfusion, minimizing and/or eliminating tissue necrosis, and facilitating overall tissue healing.

As described herein, a preferred embodiment comprises a vasoactive composition for improving tissue perfusion comprising a phosphodiesterase inhibitor, a calcium channel blocker, a nitric oxide producer, an α-adrenergic antagonist, and a carrier.

A preferred embodiment further comprises methods of preparing a vasoactive composition for improving tissue perfusion comprising a phosphodiesterase inhibitor, a calcium channel blocker, a nitric oxide producer, an α-adrenergic antagonist, and a carrier.

Yet another preferred embodiment comprises methods of using a vasoactive composition for improving tissue perfusion, wherein the composition comprises a phosphodiesterase inhibitor, a calcium channel blocker, a nitric oxide producer, an α-adrenergic antagonist, and a carrier.

While multiple embodiments are disclosed, still other embodiments of the compositions and methods of making and using the compositions may be apparent to those skilled in the art from the following detailed description, which shows and describes illustrative embodiments of the compositions as well as methods of preparation and use. Accordingly, the figures and detailed description are to be regarded as illustrative in nature and not restrictive.

BRIEF DESCRIPTION OF THE FIGURES

FIG. 2 indicates that the compositions of the present application performed significantly better than a topical nitroglycerin composition and Vaseline, and in several instances significantly better than even the negative control.

FIG. 3 shows a statistically significant improvement in perfusion compared to the control treatment.

Figure 1A:
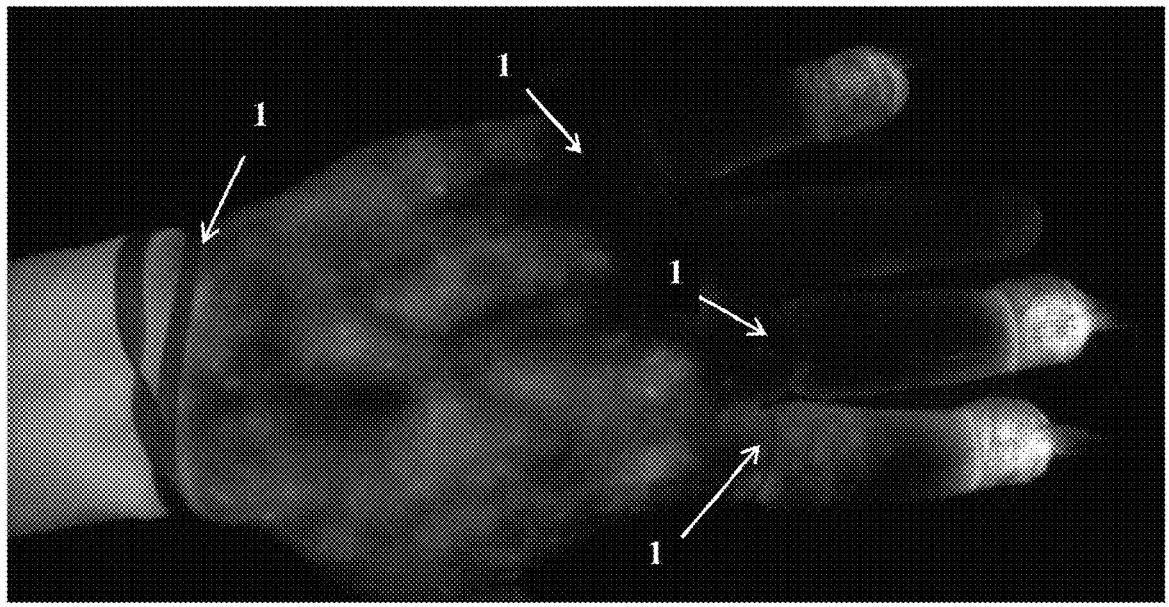
FIG. 1A shows an in vivo, ischemic hand model evaluating the compositions of the application by first applying tourniquets 1 to the wrist and to the index finger, the long finger, and the small finger in order to constrict blood flow. A tourniquet was not applied to the ring finger. The contrast imaging depicted in FIG. 1A shows the reduction in blood flow throughout the hand; white shading indicates blood flow.

Various embodiments of the present invention will be described in detail with reference to the figures. Reference to various embodiments does not limit the scope of the invention. Figures represented herein are not limitations to the various embodiments according to the invention and are presented for exemplary illustration of the invention.

DETAILED DESCRIPTION

The embodiments of this invention are not limited to particular systems and methods for preventing necrosis and facilitating tissue healing. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 11/2, and 43/4 This applies regardless of the breadth of the range.

So that the present application may be more readily understood, certain terms are first defined. Unless defined otherwise, all technical and scientific terms used herein have the same meaning as commonly understood by one of ordinary skill in the art to which embodiments of the present application pertain. Many methods and materials similar, modified, or equivalent to those described herein can be used in the practice of the embodiments of the present application without undue experimentation, the preferred materials and methods are described herein. In describing and claiming the embodiments of the present application, the following terminology will be used in accordance with the definitions set out below.

The term "and/or" means any one of the items, any combination of the items, or all of the items with which this term is associated.

The term "about," as used herein, refers to variation in the numerical quantity that can occur, for example, through typical measuring techniques and equipment, with respect to any quantifiable variable, including, but not limited to, mass, volume, time, temperature, flow, perfusion, microbial population, etc. Further, given typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about," the claims include equivalents to the quantities.

The term "weight percent," "wt. %," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt. %," etc.

As used herein, the term "functional ingredient" includes a material that when dispersed or dissolved in a use and/or concentrate solution, such as an aqueous solution, provides a beneficial property in a particular use.

As used herein, the term "anionic surfactant" refers to surfactants which possess a negative charge on their hydrophilic end.

The term "nonionic surfactant" refers to surfactants which have no charge on their hydrophilic end, which helps make them excellent emulsifiers.

As used herein, the term "cationic surfactant" refers to surfactants which possess positively charged ends. Some cationic surfactants have antimicrobial characteristics.

The term "amphoteric surfactant" as used herein refers to surfactants having both a positive and a negative charge on their hydrophilic end, typically giving the surfactants a net charge of zero. Amphoteric surfactants can beneficially serve as coupling agents, holding surfactants, solvents, and other components in a composition together.

The term "carrier" as used herein refers to diluents, adjuvants, excipients, vehicles, and other agents with which the compositions of the present application are administered. As used herein, the term "base" refers to diluents, adjuvants, excipients, vehicles, and other agents which may contribute to the volume of the composition and may aid in the ease of administration of the composition of the application. A carrier may carry, encompass, protect, cause the extended release of, or otherwise facilitate the administration of one or more components of the compositions of the application. As such, some carriers may also function as a base. Bases and carriers are preferably pharmaceutically acceptable, meaning they are suitable for pharmaceutical administration without undue toxicity, incompatibility, instability, irritation, allergic response and the like. A "pharmaceutically acceptable salt" can be derived from pharmaceutically acceptable inorganic or organic bases and from pharmaceutically acceptable inorganic and organic acids, which are known in the art and can be derived by one of ordinary skill in the art. Examples of pharmaceutically acceptable carriers include but are not limited to sugars, starches, cellulose, excipients, oils, glycols, polyols, esters, agar, and buffering agents. The above are non-limiting examples of carriers. Pharmaceutically acceptable carriers and bases other than those listed herein may be easily formulated by those of ordinary skill in the art.

The term "tissue site" as used herein broadly refers to a wound or defect located on or within tissue, including but not limited to, bone tissue, adipose tissue, muscle tissue, neural tissue, dermal tissue, vascular tissue, connective tissue, mucosa, cartilage, tendons, or ligaments. A wound may include, for example, chronic, acute, traumatic, sub-acute, and dehisced wounds, partial-thickness burns, ulcers (such as diabetic, pressure, or venous insufficiency ulcers), flaps, and grafts. The term "tissue site" may also refer to areas of any tissue that are not necessarily wounded or defective, but are instead areas in which it may be desirable to add or promote the growth of additional tissue. For example, reduced pressure may be used in certain tissue areas to grow additional tissue that may be harvested and transplanted to another tissue location.

The term "topical" application refers to application to skin, epidermis, dermis, mucosa or tissue site, and application to such tissue sites may include application adjacent to or within the tissue site.

As used herein, the terms "sterile," "sterilization," relate to the "sterility assurance level" for medical devices. A sterile medical device or other compound, component, or product used in a sterile surgical environment is one that is free of viable microorganisms. This can be achieved through a terminal sterilization process, sterilization of components (followed by sterile filtration and aseptic filling into a sterilized container), and/or a combination of chemical/physical sterilization and aseptic processing. Sterility in this context is defined by the probability of a viable microorganisms on the product after it has been sterilized, i.e. the sterility assurance level (SAL). When selecting a threshold of sterility, the most rigorous SAL should be selected and used based on the ability of the product or device to function after it undergoes the sterilization process. SAL is typically expressed as 10-" with $10^{-3}$ as the typical minimum SAL allowable for some medical devices depending on their intended use or their ability to withstand a terminal sterilization process. An SAL of $10^{-6}$ is frequently used for the terminal sterilization of medical devices, and represents a probability of 1 in 1,000,000 of finding a non-sterile unit. More specifically, a SAL of $10^{-6}$ or greater is used for products intended to come into contact with breached skin or compromised tissue, invasive products that enter normally sterile tissue, products with claims of sterile fluid pathways, and surgically implanted devices. An SAL of $10^{-3}$ is allowed for products not intended to come into contact with breached or compromise skin, or topical products that come into contact with intact skin. Thus, according to the compositions of the present application, which are intended to come into contact with breached and/or compromise tissue and/or skin, an SAL of $10^{-6}$ is preferred.

Various other terms are defined herein below.

VasoActive Compositions

The present application provides a composition and methods of use thereof that increases tissue blood flow via activity on arteries, arterioles, capillaries, venules, veins and the rheologic property of blood. In an embodiment, the compositions of the application comprise at least one of each of a phosphodiesterase inhibitor, a calcium channel blocker, a nitric oxide producer, and an alpha-adrenergic antagonist, together with a base/carrier.

In a preferred embodiment, the phosphodiesterase inhibitor (PDI) is pentoxifylline, the calcium channel blocker (CCB) is magnesium sulfate, the nitric oxide (NO) producer is nitroglycerin, the alpha-adrenergic antagonist is chlorpromazine, and the base is petroleum. In a further embodiment, the composition comprises about 320 mg of the phosphodiesterase inhibitor, about 4 mEq of the calcium channel blocker, about 400 mg of the alpha-adrenergic antagonist, and about 300 mg of the nitric oxide producer, per every 1 ml of the base.

The compositions of the present application may be prepared according to the exemplary ranges in Tables 1A-1B.

TABLE 1A

| Component | Example Range 1 wt. % | Example Range 2 wt. % | Example Range 3 wt. % |
|---|---|---|---|
| PDI | 0.1-30 | 5-25 | 10-20 |
| CCB | 5-35 | 10-30 | 15-25 |

TABLE 1A-continued

| Component | Example Range 1 wt. % | Example Range 2 wt. % | Example Range 3 wt. % |
| --- | --- | --- | --- |
| NO Producer | 0.1-30 | 5-25 | 10-20 |
| α-adrenergic Antagonist | 0.1-30 | 5-25 | 10-20 |
| Base/Carrier | 15-75 | 25-50 | 30-40 |

TABLE 1B

| Component | Example Range 1 Raw Qty. | Example Range 2 Raw Qty. | Example Range 3 Raw Qty. |
| --- | --- | --- | --- |
| PDI | 1-500 mg | 10-400 mg | 20-360 mg |
| CCB | 1-50 mEq | 1-40 mEq | 1-20 mEq |
| NO Producer | 1-450 mg | 5-400 mg | 10-350 mg |
| α-adrenergic Antagonist | 1-500 mg | 15-475 mg | 40-450 mg |
| Base/Carrier | 0.1-100 ml | 0.1-50 ml | 0.5-30 ml |

Phosphodiesterase Inhibitor

Phosphodiesterase inhibitors (PDE inhibitors) are compounds which inhibit phosphodiesterase enzymes (PDEs). PDE inhibitors prevent the inactivation of cyclic adenosine monophosphate (cAMP) and cyclic guanosine monophosphate (cGMP) by the various PDE subtypes. Phosphodiesterase inhibitors are classified according to the type of PDE which is inhibited, namely nonselective PDE inhibitors, PDE1 selective inhibitors, PDE2 selective inhibitors, PDE3 selective inhibitors, PDE4 selective inhibitors, PDE5 selective inhibitors, PDE7 selective inhibitors, and PDE10 selective inhibitors.

Any suitable phosphodiesterase inhibitor may be used, including without limitation, vinpocetine, erythron-9-(2-hydroxy-3-nonyl) adenine, (2-[(3,4-dimethoxyphenyl)methyl]-7-[(1R)-1-hydroxyethyl]-4-phenylbutyl]-5-methyl-imidazo[5,1-f][1,2,4]triazin-4 (1H)-one), oxindole, (9-(6-Phenyl-2-oxohex-3-yl)-2-(3,4-dimethoxybenzyl)-purin-6-one), inamrinone, amrinone, anagrelide, cilostazol, mesembrenone, rolipram, ibudilast, piclamilast, luteolin, drotaverine, roflumilast, apremilast, crisaborole, sildenafil, dipyridamole, quinazoline, papaverin, and mixtures thereof.

In a preferred embodiment, the phosphodiesterase inhibitor is a nonselective/nonspecific phosphodiesterase inhibitor.

In a further preferred embodiment, the nonspecific phosphodiesterase inhibitor is a methylxanthine phosphodiesterase inhibitor. Examples of suitable methylated xanthines and derivatives include caffeine, aminophylline, 2-isobutyl-1-methylxanthine, paraxanthine, pentoxifylline, lisofylline, propentofylline, cilostazol, theobromine, and/or theophylline. In a preferred embodiment, the phosphodiesterase inhibitor is pentoxifylline.

The composition preferably comprises at least one phosphodiesterase inhibitor, and may include additional phosphodiesterase inhibitors as needed, for example two, three, four, or more phosphodiesterase inhibitors.

In a preferred embodiment, the phosphodiesterase inhibitor is present in amounts ranging from about 1 mg to about 500 mg, more preferably from about 5 mg to about 450 mg, about 10 mg to about 425 mg, about 15 mg to about 400 mg, about 20 mg to about 360 mg, or about 25 mg to about 350 mg.

The phosphodiesterase inhibitor may also be expressed in terms of weight percent of the composition. For example, the phosphodiesterase inhibitor is preferably present in amounts of between about 0.1 wt. % and about 30 wt. %; more preferably between about 5 wt. % and about 25 wt. %; most preferably between about 10 wt. % and about 20 wt. %.

Calcium Channel Blocker

Calcium channel blockers (CCBs) are compounds which bind to and block the L-type calcium channel, which in turn causes peripheral arterial vasodilation. CCBs can be divided into three primary classes, namely dihydropyridines which function as vasodilators, phenylalkylamines which act as myocardial depressants, and benzothiazepines which are more moderate vasodilators and myocardial depressants.

The composition may comprise any suitable calcium channel blocker, including without limitation nifedipine, clevidipine, nitrendipine, nicardipine, lercarnidipine, amlodipine, bepridil, felodipine, nisoldipine, diltiazem, verapamil, gallopamil, and/or magnesium and salts thereof. In a preferred embodiment, the calcium channel blocker is magnesium sulfate.

The composition preferably comprises at least one calcium channel blocker, and may include additional calcium channel blockers as needed, for example two, three, four, or more calcium channel blockers.

The calcium channel blocker may be present in amounts ranging from about 1 mEq to about 50 mEq, including, for example, about 2, 3, 4, 5, 6, 7, 8, 9, 10, 11, 12, 13, 14, 15, 16, 17, 18, 19, 20, 21, 2, 2, 24, 25, 26, 27, 28, 29, 30, 31, 32, 33, 34, 35, 36, 37, 38, 39, 40, 41, 42, 43, 44, 45, 46, 47, 48, 49, or about 50 mEq.

The calcium channel blocker may also be expressed in terms of weight percent of the composition. For example, the calcium channel blocker is preferably present in amounts of between about 5 wt. % and about 35 wt. %; more preferably between about 10 wt. % and about 30 wt. %; most preferably between about 15 wt. % and about 25 wt. %.

Nitric Oxide Producer

The compositions of the application preferably include at least one nitric oxide producer/releaser. Nitric oxide (NO) is a free radical which can be naturally produced endemically, and contributes to a variety of key functions including neurotransmission, neuronal communication, vasodilation, inflammation, wound healing, and others. Compositions which produce or release nitric oxide may be organic or synthetic. Suitable classes of NO donors may include without limitation, nitrate/nitrite/nitroso compounds, N-diazeniumdiolates, S-nitrosothiols, and others.

Organic nitrates and nitrites include, for example, nitroglycerin, isosorbide dinitrate, isosorbide mononitrate, and isoamyl nitrite. These compounds release NO upon exposure to particular endogenous enzymes. Relatedly, sodium nitroprusside (SNP) is an addition NO— based compound, although SNP has a relatively short half-life.

Diazeniumdiolates (NONOates) are another class of NO donors that may be used. NONOates carry an [N(O—)N—O] group on a nucleophile adduct, usually an amine. Further, NONOates decompose spontaneously in solution at physiological pH and temperature to generate NO. Examples of suitable diazeniumdiolates may include diethylamine/NO, V—PYRRO/NO, and/or spermine/NO, and others. Another suitable example of a nitric oxide donor is hydralazine. Hydralazine also functions as a potassium channel agonist.

S-nitrosothiols (RSNOs) are adducts of R—SH and NO, whose rate of NO release is based on a variety of factors, such as metal ions, reducing agents, enzymes, light, heat, and pH. Beneficially, RSNOs have the capacity for long lasting release of NO. Suitable S-nitrosothiols may include, for example, S-nitrosoglutathione, S-nitroso-N-acetylcysteine, and/or S-nitroso-acetylpencillamine, and others.

In a preferred embodiment, the nitric oxide producer is nitroglycerin or 1,2,3-trinitroxypropane.

The nitric oxide producer of the composition may further comprise a vehicle for transportation and delivery of the nitric oxide producer. Such vehicles may include without limitation gold nanoparticles (GNP), silica nanoparticles, polymeric vehicles, dendrimers, micelles, and/or lipid-based nanocarriers. Further discussion of suitable vehicles can be found in Liang et al., Nitric Oxide Generating/Releasing Materials, FUTURE SCI OA 1 (1) (2015), which is herein incorporated by reference in its entirety.

The composition preferably comprises at least one nitric oxide producer/releaser, and may include additional nitric oxide producers/releasers as needed, for example two, three, four, or more nitric oxide producers/releasers.

If additional vasodilation is required, the composition may include one or more additional types of vasodilators, such as prostaglandin, sildenafil citrate, sildenafil, tadalafil, bosentan, or any other pulmonary vasodilator, acetylcholine, benazepril, captopril, enalapril, fosinopril, lisinopril, moexipril, perindopril, quinapril, ramipril, trandolapril, or any suitable angiotensin converting enzyme (ACE) inhibitor, azilsartan, candesartan, eprosartan, irbesartan, telmisartan, valsartan, losartan, olmesartan, or any suitable angiotensin receptor blocker (ARB), amlodipine, clevidipine, diltiazem, felodipine, isradipine, nicardipine, nimodipine, nisoldipine, verapamil, or any suitable calcium channel blocker (CCB) including those described herein, isosorbide mononitrate, isosorbide dinitrate, hydralazine, minoxidil, fenoldopam, nitroprusside, or any other suitable nitrate, and combinations thereof.

In a preferred embodiment, the nitric oxide producer and optionally additional vasodilators are present in amounts ranging from about 1 mg to about 450 mg, more preferably from about 5 mg to about 400 mg, or about 10 mg to about 350 mg.

The nitric oxide producer and optionally additional vasodilators may also be expressed in terms of weight percent of the composition. For example, the nitric oxide producer is preferably present in amounts of between about 0.1 wt. % and about 30 wt. %; more preferably between about 5 wt. % and about 25 wt. %; most preferably between about 10 wt. % and about 20 wt. %.

Alpha-Adrenergic Antagonist

Alpha-adrenergic antagonists, also known as alpha blockers, function to keep norepinephrine from tightening the muscles in the walls of arteries and veins, which causes these vessels to remain open and relaxed. This results in improved blood flow and lower blood pressure. Alpha blockers may be either short-acting or long-acting. Alpha blockers may be categorized as an $\alpha_1$ blocker, an $\alpha_2$ blocker, a nonselective blocker having both $\alpha_1$ and $\alpha_2$ activity, or an $\alpha$ block with some $\beta$ activity.

Examples of suitable alpha-adrenergic antagonists include without limitation, doxazosin, prazosin, terazosin, phenoxybenzamine, phentolamine, tolazoline, trazodone, alfuzosin, tamsulosin, silodosin, atipamezole, idazoxan, mirtazapine, yohimbe, carvedilol, chlorpromazine, and/or labetalol.

In a preferred embodiment, the alpha-adrenergic antagonist is chlorpromazine.

The composition preferably comprises at least one alpha blocker, and may include additional alpha blockers as needed, for example two, three, four, or more alpha blockers.

In a preferred embodiment, the alpha blocker is present in amounts ranging from about 1 mg to about 500 mg, more preferably from about 15 mg to about 475 mg, or about 40 mg to about 450 mg.

The alpha blocker may also be expressed in terms of weight percent of the composition. For example, the alpha blocker is preferably present in amounts of between about 0.1 wt. % and about 30 wt. %; more preferably between about 5 wt. % and about 25 wt. %; most preferably between about 10 wt. % and about 20 wt. %.

Base/Carrier

In addition to the aforementioned components, the compositions of the application preferably further comprise a base or carrier, which is any suitable substrate used to facilitate the delivery of the compositions described herein. The base/carrier may be used to control and/or time the release of the composition, and to that end may be released by diffusion, or triggered by a stimulus such as changes in pH, heat, light, etc. Further, the base/carrier may be attached to the compositions described herein by a variety of means including simple mixing, adsorption, integration into the bulk structure, encapsulation, and/or covalent bonding. The base/carrier may also be antibacterial-based and/or petroleum-based. Preferably the base/carrier is a pharmaceutically acceptable base/carrier.

The base/carrier may comprise lipids/phospholipids, alcohols, glycols, water, and/or other solvents. In a preferred embodiment, the base/carrier is petroleum or vaseline.

The base/carrier may also comprise an organogel. For example, puronic lecithin organogels (PLO gels) are lecithin-based organogels which can be used to enhanced transdermal permeability of compositions. Further discussion of organogels and their use as a carrier is discussed in Alsaab et al., *Organogels in Drug Delivery: A Special Emphasis on Pluronic Lecithin Organogels*, J. PHARM. PHARM. SCI. 19 (2): 252-73 (2016), which is herein incorporated by reference in its entirety.

The base/carrier may also comprise or be used together with the nitric oxide carriers described herein, such as gold nanoparticles (GNP), silica nanoparticles, polymeric vehicles, dendrimers, micelles, and/or lipid-based nanocarriers.

The composition preferably comprises at least one base/carrier, and may include additional bases/carriers as needed, for example two, three, four, or more bases/carriers.

In a preferred embodiment, the base/carrier is present in amounts ranging from about 0.1 ml to about 100 ml, more preferably from about 0.1 ml to about 50 ml, or about 0.5 ml to about 30 ml.

The base/carrier may also be expressed in terms of weight percent of the composition. It should be understood that the amount by weight may depend on the density of the selected carrier. For example, the base/carrier is preferably present in amounts of between about 15 wt. % and about 75 wt. %; more preferably between about 25 wt. % and about 50 wt. %; most preferably between about 30 wt. % and about 40 wt. %.

Penetration Enhancers

The compositions of the application may further comprise one or more penetration enhancers, particularly a percutaneous and/or transdermal penetration enhancer.

For example, a chemical penetration enhancer may be used as part of the compositions of the application. There are a variety of chemical substances which temporarily diminish the barrier of the skin, including without limitation chlorpromazine hydrochloride, oleic acid, polysorbate 80, propylene glycol, sulphoxides such as dimethyl sulphoxides (DMSO), azone (1-dodecylazacycloheptan-2-one, laurocapran), pyrrolidones, fatty acids such as lauric acid, myristic acid, capric acid etc., glycols such as propylene glycol, diethylene glycol, tetraethylene glycol, etc., essential oils, terpenes, terpenoids, oxazolidinones, and/urea. Further discussion of chemical transdermal penetration enhancers can be found in Pathan & Setty, *Chemical Penetration Enhancers for Transdermal Drug Delivery Systems*, TROP. J. PHARM. RES. 8 (2): 173-79 (2009), which is herein incorporated by reference in its entirety.

The chemical penetration enhancer may further comprise a surfactant, such as a nonionic surfactant, cationic surfactant, zwitterionic surfactant, and others. Broadly, examples of suitable anionic surfactants include carboxylates, sulfates, sulfonates, and/or phosphate esters. More specifically, suitable anionic surfactants may include, without limitation sodium dodecylsulfate (SDS), sodium lauryl sulfate (SLS), sodium dodecyl sulfate (SDS), and mixtures thereof.

Suitable cationic surfactants may include without limitation benzalkonium chloride (BZK), cetyltrimethylammonium bromide (CTAB), cetrimide, dodecylamine, cetylpyridinium chloride, and mixtures thereof.

Suitable nonionic surfactants may include without limitation polyethylene glycol sorbitan monooleate (e.g. Tween 80), polyoxyethylene alkyl ether, polyoxyethylene monoalkyl carboxylate, sorbitan monolaurate, polyoxyethylene-2-oleyl ether, polyoxyethylene sorbitan monoesters, polyoxyethylene alkyl esters, polysorbates, polyoxyethylene nonylphenol, sorbitan monopalmitate, sorbitan monolaurate, EO/PO copolymers, EO polymers, PO polymers, pluronics, reverse pluronics, and mixtures thereof.

Suitable zwitterionic surfactants may include, without limitation, dodecyl betaine, hexadecylbetaine, hexadecylsulfobetaine, N, N-dimethyl-N-dodecyl amine oxide, dodecyl trimethylammonium bromide, and mixtures thereof.

Further discussion of surfactants as penetration enhancers can be found in Som et al., *Status of Surfactants as Penetration Enhancers in Transdermal Delivery*, J. PHARM. BIOALLIED SCI. 4 (1): 2-9 (2012), and in PERCUTANEOUS PENETRATION ENHANCERS: CHEMICAL METHODS IN PENETRATION ENHANCEMENT (Dragicevic & Maibach, Ed.) (2015), which are herein incorporated by reference in their entirety.

Additional Functional Ingredients

The components of the composition can further be combined with various additional functional components. The functional ingredients provide desired properties and functionalities to the compositions. For the purpose of this application, the term "functional ingredient" includes a material that when dispersed or dissolved in a use and/or concentrate solution, such as an aqueous solution, provides a beneficial property in a particular use. Some particular examples of functional materials are discussed in more detail below, although the particular materials discussed are given by way of example only, and that a broad variety of other functional ingredients may be used.

Depending upon the use of the composition, the composition may comprise additional functional ingredients such as moisturizers or emollients (e.g. glycerol, liquid paraffin, purified lanolin white ointment, ointment base), mineral oil, silicone oils, fragrances, botanical extracts, collagen, gelatin, hydrolysate, preservatives such as chelating agents (e.g. ethylenediaminetetraacetic acid (EDTA), diethylene triamine pentaacetic acid (DTPA, catechins, etc.), sodium benzoate, potassium sorbate, or sodium nitrate, antimicrobial agents such as cationic surfactants (especially quaternary ammonium compounds), aloe vera, ashitaba, chlorhexidine, copper, dispersin B, cinnamon oil, clove oil, eucalyptus oil, tea tree oil, gentamicin, lactoferrin, lysostaphin N-halamines, nitric oxide, oleic acid, PLUNC protein, polyhexanide biguanide (PHMB), bacteriocin, selenium, silver compound, triclosan, zinc, and combinations thereof.

The compositions disclosed herein may additionally comprise conventional adjuvants such as propionic acid, propylene glycol, conventional buffers, preservatives, hydrophilic emulsifiers, lipophilic emulsifiers, perfumes, emollients, deodorants, humectants and the like. Colorants may also optionally be added in the compositions disclosed herein. Adjuvants which would be harmful to a tissue site or surrounding skin should be avoided, as well as those adjuvants which may react with and/or adversely reduce the effectiveness of the composition.

The compositions may further comprise an anesthetic, such as lidocaine, morphine, barbiturates, benzodiazepines, etomidate, ketamine, propofol, dibucaine, dyclonine, prilocaine, articaine, bupivacaine, etidocaine, mepivacaine, chloroprocaine, procaine, tetracaine, benzocaine, and mixtures thereof.

The additional functional ingredients, where present, can comprise between 0 wt. % and 99 wt. % of the composition, for example between about 1 wt. % to about 90 wt. %, about 10 wt. % to about 80 wt. %, about 20 wt. % to about 70 wt. %, about 30 wt. % to about 60 wt. %, about 40 wt. % to about 50 wt. % of the composition.

Methods of Administering

In an embodiment, the compositions of the application are prepared by mixing at least one of each of a phosphodiesterase inhibitor, a calcium channel blocker, a nitric oxide producer, and an alpha-adrenergic antagonist together with a base/carrier.

The compositions according to the present application may be provided as a lotion, cream, gel, stick, emollient, spray, topical ointment, oozing ointment, paste, powder, film-forming product, a solid composition, a liquid concentrate, a liquid dilution, as part of a patch, particularly an extended release patch, an instillation composition, wherein the composition is delivered to a target site by continuous and/or periodic instillation, as part of negative pressure therapy, and/or as part of a bandage/dressing.

For example, in an embodiment the invention comprises a composition for treating skin or tissue comprising a therapeutically effective amount of the phosphodiesterase inhibitor, calcium channel blocker, nitric oxide producer, and alpha-adrenergic antagonist together with a base carrier. In such an embodiment, the composition is therapeutically effective at the target depth and location, for example a target epidermis layer, dermis layer, mucosal layer and/or muscle tissue, including intraperitoneal tissue, intraabdominal tissue, tissue connected with venous stasis ulcers, and/or breast tissue. Administration may be topical, subcutaneous, transdermal, intramucosal, intramuscular, intradermal, and where appropriate epicutaneous and/or enteral.

In a preferred embodiment, upon administration the compositions of the present application have a half-life of between about 6 and 20 hours. As such, administration of the composition may occur less frequently than existing products. In an embodiment, reapplication of the composition may occur during a desired time frame, for example between about once every 30 minutes to once a week, including once an hour, twice a day, three times a day, four times a day, five times a day, six times a day, every other day, twice a week, three times a week, once a week, twice a month, and/or once a month.

Where the composition comprises a skin ointment or cream, the method of administration may comprise a method of treating skin or tissue comprising applying to the skin or tissue an ointment or cream as described herein, wherein the ointment or cream provides a therapeutically effective amount of the composition at the target depth or location, and wherein the ointment or cream improves tissue perfusion and inhibits the incidence of necrosis.

Where the composition comprises a spray or foam, the method of administration may comprise a method of treating skin or tissue comprising spraying the skin or tissue with a sprayable or foaming composition as described herein, wherein the spray or foam provides a therapeutically effective amount of the composition at the target depth or location, and wherein the spray or foam improves tissue perfusion and inhibits the incidence of necrosis.

Where the composition is integrated into a wound dressing or patch, the composition further comprises wound dressing or patch materials, such as gauze, impregnated gauze, adaptic gauze®, xeroform gauze®, transparent film dressings (e.g. thing flexible transparent sheets with adhesive backing polyurethane or co-polyester), tegaderm®, foam dressings (e.g. dressings made from a polyurethane base), hydrogels (e.g. complex hydrophilic cross-linked polymers together with a water base available as a free-flowing amorphous or fixed flexible sheet form), regranex®, flexigel, hydrocolloids (e.g. dressings containing an inner layer which is self-adhesive, gel forming, and composed of hydrophilic colloid particles such as CMC, pectin, gelatin, or an elastomer), hydrofibers (dressings made from sodium CMC which interact with serum or exudates to form a gel), hydroconductive dressings, drawtex®, oxidated regenerated cellulose and collagen (ORC), silver dressings, polyhexamethylene biguanide (PHMB), honey dressings, iodine dressings, charcoal dressings, and so forth. Further discussion of wound dressings and the relative advantages and disadvantages of each type of dressing can be found in Sood et al., *Wound Dressings and Comparative Data*, ADV. WOUND CARE 3 (8), 511-529 (2014), which is herein incorporated by reference in its entirety.

In such an embodiment, the base and material of the wound dressing preferably allow for gaseous exchange while remaining impenetrable to microorganisms. Further, when the composition is provided as part of a wound dressing or patch, the method of administration may comprise a method of treating skin or tissue comprising imbibing a wound dressing or patch material as described herein with the compositions of the application, and applying the wound dressing or patch material to a target skin or tissue surface, wherein the wound dressing or patch material provides a therapeutically effective amount of the composition at the target skin or tissue surface and depth thereof, and wherein the wound dressing or patch material imbibed with the composition improves tissue perfusion and inhibits the incidence of necrosis.

In a still further embodiment, the compositions of the present application are provided as part of a kit. The kit preferably comprises a composition according to present application comprising phosphodiesterase inhibitor, a calcium channel blocker, a nitric oxide producer, an alpha-adrenergic antagonist, and a base/carrier; a container or solid support for the composition, instructions for using the kit, and a container for the kit.

In an embodiment the container or solid support for the composition comprises a pouch, a tube, a cannister, a plastic bag, an envelope, or other encasing suitable for the form of the composition. For example, where the composition is a cream or a gel, the container for the composition may include a tube with a screw top. As a further example, where the composition is provided as a foam or a spray, the container for the composition may include an aerosol or non-aerosol cannister. As a third example, where the composition is imbibed in a wound dressing or patch, the container for the composition may include a tearable, sealed plastic bag or envelope.

In an embodiment, the instructions for using the kit may include instructions for applying the composition to a target skin or tissue surface.

In an embodiment, the container for the kit may comprise a container large enough to hold a desired number of units of the composition, e.g. a desired number of tubes, cannisters, or wound dressings, as well as the instructions. The container for the kit may be a cardboard box, a plastic box, or other suitable container.

Further methods of composition delivery and treatment methods can be found in U.S. Patent Publication 2014/0276493A1, which is herein incorporated by reference in its entirety.

Examples

The following non-limiting examples are provided to further illustrate the present invention.

EXAMPLE 1

A composition was prepared by admixing the components in Table 2 to form a simple mixture. This composition was compared to a nitro paste composition, Vaseline, and a negative control (no treatment).

TABLE 2

| Component | Quantity | Wt. % |
|---|---|---|
| Pentoxifylline | 320 mg | 13.54 |
| Magnesium sulfate | 493 mg | 20.85 |
| Nitroglycerin | 300 mg | 12.70 |
| Chlorpromazine | 400 mg | 16.93 |
| Petroleum Jelly | 1 ml | 35.98 |

To evaluate the impact on tissue perfusion, blood flow was restricted to a human hand using tourniquets 1 placed on the wrist and one each proximal phalanx just distal to the metacarpophalangeal joint (MCP). The tourniquets 1 were left in place until contrast imaging indicated very little blood flow throughout the hand. (See FIG. 1A where white shading indicates blood flow). After blood flow was sufficiently disrupted, nitro paste was applied to the small finger, Vaseline was applied to the long finger, and the composition of Table 2 was applied to the index finger. The ringer finger was left untreated as the negative control.

Figure 1B:
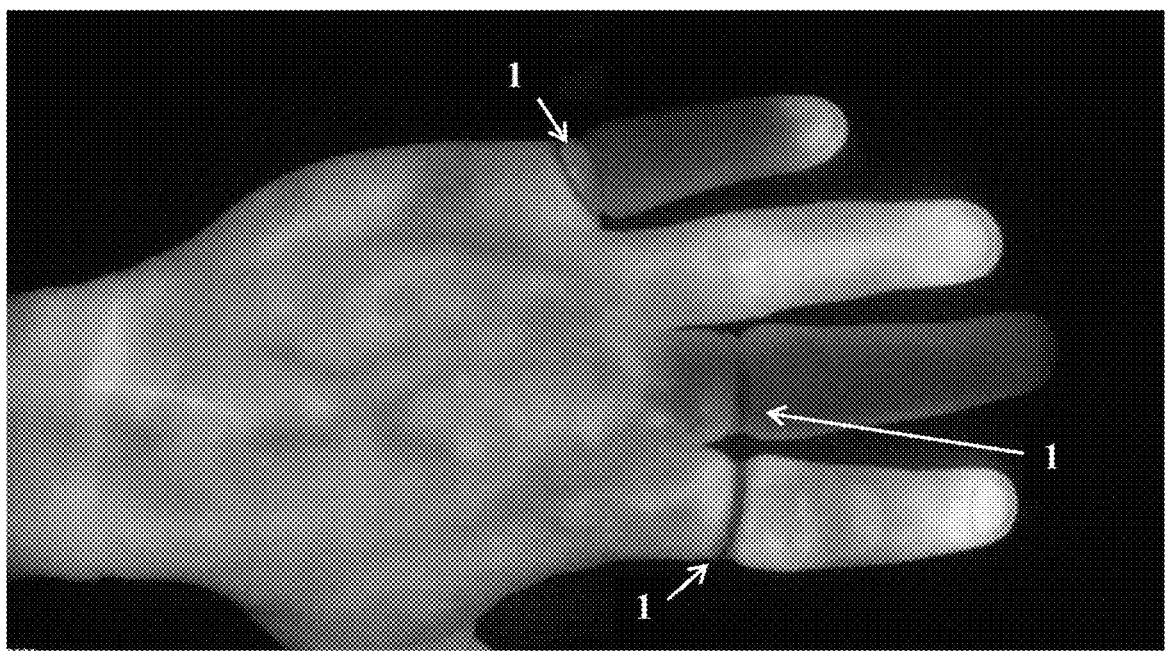
FIG. 1B shows an in vivo, ischemic hand model evaluating the compositions of the application in comparison to topical nitroglycerin, Vaseline, and a negative control, wherein the tourniquets 1 on the wrist and negative control are removed to evaluate the restoration of blood flow to the tissue of each finger. The composition of the application was applied to the index finger, Vaseline was applied to the long finger, the ring finger is the negative control meaning no treatment was applied to the ring finger, and the small finger was given topical nitroglycerin. White shading indicates blood flow.

After application of the relevant compositions, the tourniquets on the wrist and ring finger were removed to allow blood flow to return. The tourniquets 1 were left on the small, long, and index fingers to simulate a tissue with low perfusion (e.g. due to injury, disease, surgery, etc.). Contrast imaging was then used to assess the degree of blood flow in each of the fingers. The results are shown in FIG. 1B; white shading indicates blood flow.

Figure 2:
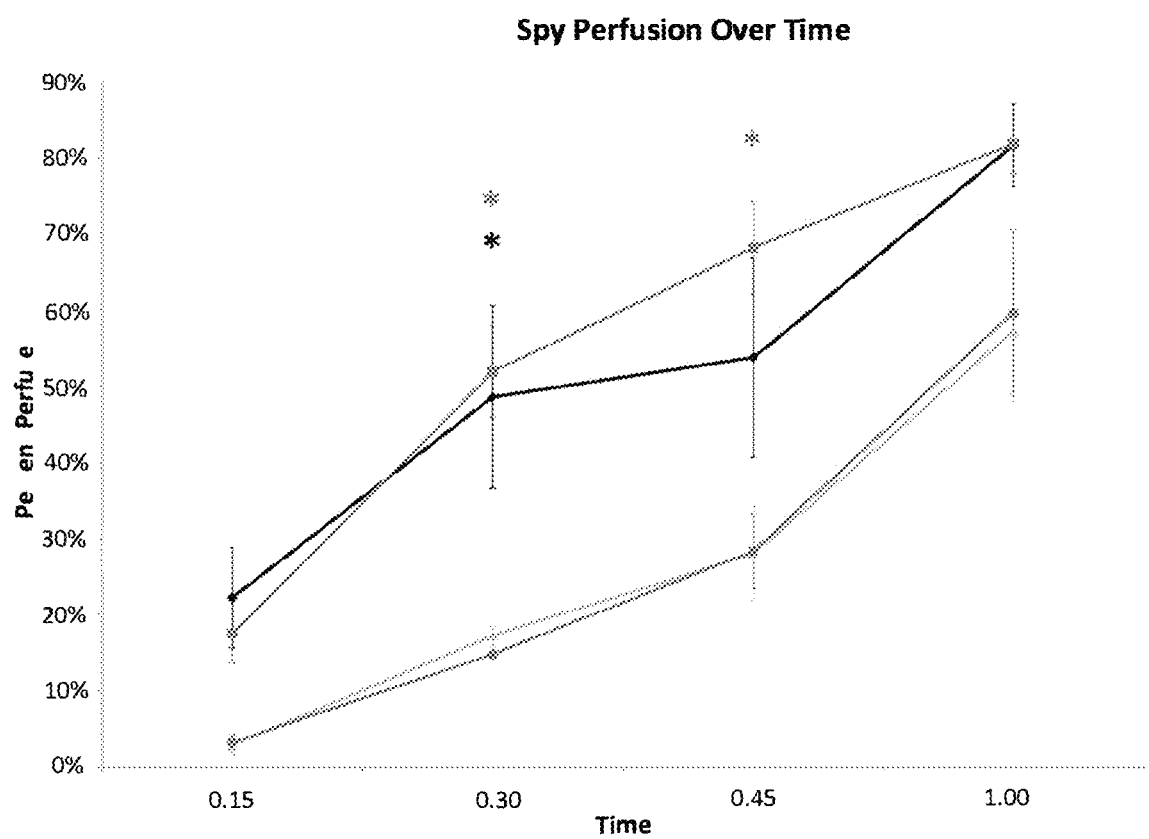
FIG. 2 depicts the data from the in vivo, ischemic hand model in terms of skin perfusion over time. The negative control data points are represented by diamonds, Vaseline treatment data points are represented by triangles, nitro paste treatment data points are represented by circles, and the composition of the invention is represented by squares.

FIG. 2 is a graph depicting the results of this evaluation in terms of perfusion over time. In FIG. 2, the negative control data points are represented by diamonds, Vaseline treatment data points are represented by triangles, nitro paste treatment data points are represented by circles, and the composition of Table 2 is represented by squares. FIG. 2 shows that the compositions of the application facilitate blood flow significantly better than either nitro paste or Vaseline, and at some points facilitate blood flow significantly better than even the negative control. Those points are represented by stars in FIG. 2.

EXAMPLE 2

The composition of Table 2 was again prepared and applied intra-operatively to a tissue sample. Two sections of abdominal skin and fat were dissected during a breast reconstruction procedure. The separate sections of tissue were then treated with Vaseline as the control and the composition of Table 2 was applied to a separate section of abdominal tissue.

Figure 3:
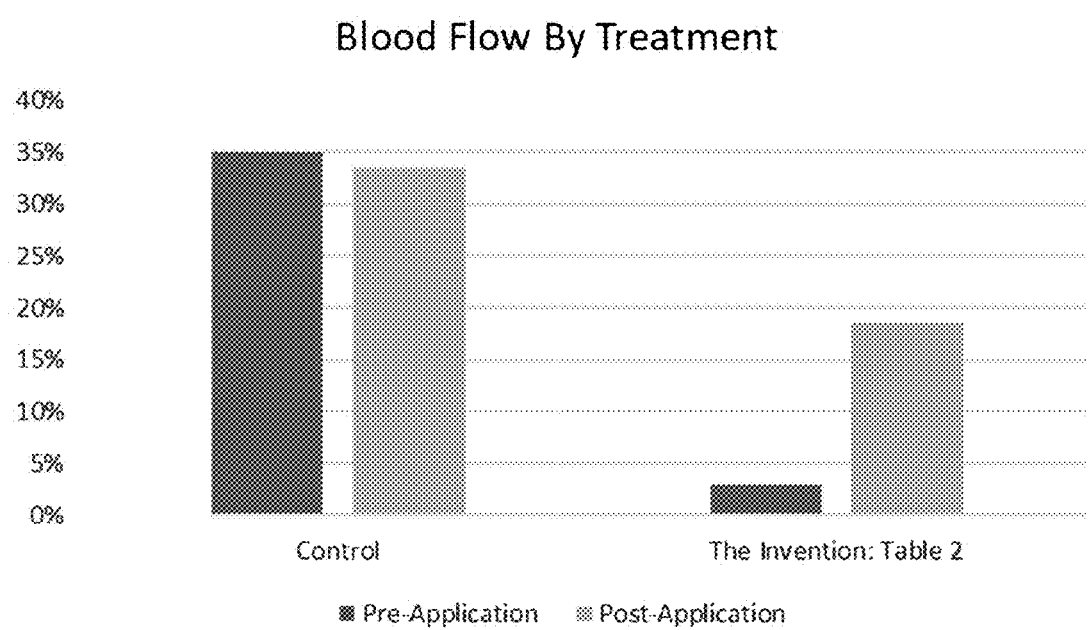
FIG. 3 graphically depicts an evaluation of the compositions of the present application in comparison to a control, wherein blood flow is evaluated before treatment and after treatment of either a control or the compositions of the application.

Blood flow was assessed with a cutaneous angiogram both before and after treatment with the control and the composition of Table 2. Contrast imaging was used to assess the degree of blood flow in each of the tissue sections. The data for this analysis is shown graphically in FIG. 3 where percent indicates the percent of white in the contrast image. FIG. 3 shows a statistically significant improvement in perfusion compared to the control.

A preferred embodiment is further defined by the following paragraphs.

A vasoactive composition for improving tissue perfusion comprising: a phosphodiesterase inhibitor; a calcium channel blocker; a nitric oxide producer; an α-adrenergic antagonist; and a carrier (hereinafter: "Comp. 1").

Comp. 1, comprising between about 0.1 wt. % and about 30 wt. % of the phosphodiesterase inhibitor (hereinafter: "Comp. 2").

Comp. 1-2, wherein the phosphodiesterase inhibitor is selected from the group consisting of vinpocetine, erythron-9-(2-hydroxy-3-nonyl) adenine, (2-[(3,4-dimethoxyphenyl) methyl]-7-[(1R)-1-hydroxyethyl]-4-phenylbutyl]-5-methyl-imidazo[5,1-f][1,2,4]triazin-4 (1H)-one), oxindole, (9-(6-Phenyl-2-oxohex-3-yl)-2-(3,4-dimethoxybenzyl)-purin-6-one), inamrinone, amrinone, anagrelide, cliostazol, mesembrenone, rolipram, ibudilast, piclamilast, luteolin, drotaverine, roflumilast, apremilast, crisaborole, sildenafil, dipyridamole, quinazoline, papaverine, caffeine, aminophylline, 2-isobutyl-1-methylxanthine, paraxanthine, pentoxifylline, lisofylline, propentofylline, cliostazol, theobromine, and/or theophylline (hereinafter: "Comp. 3").

Comp. 1-3, comprising between about 1 mEq to about 50 mEq of a calcium channel blocker (hereinafter: "Comp. 4").

Comp. 1-4, wherein the calcium channel blocker is selected from the group consisting of nifedipine, clevidipine, nitrendipine, nicardipine, lercarnidipine, amlodipine, bepridil, felodipine, nisoldipine, diltiazem, verapamil, gallopamil, and/or magnesium sulfate (hereinafter: "Comp. 5").

Comp. 1-5, comprising between about 0.1 wt. % and about 30 wt. % of the nitric oxide producer (hereinafter: "Comp. 6").

Comp. 1-6, wherein the nitric oxide producer is selected from the group consisting of nitrate compounds, nitrite compounds, nitroso compounds, organic nitrates and/or nitrates, N-diazeniumdiolates, and/or S-nitrosothiols (hereinafter: "Comp. 7").

Comp. 1-7, wherein the organic nitrates and/or nitrates comprise nitroglycerin, isosorbide dinitrate, isosorbide mononitrate, and/or isoamyl nitrite (hereinafter: "Comp. 8").

Comp. 1-8, comprising between about 0.1 wt. % and about 30 wt. % of the α-adrenergic antagonist (hereinafter: "Comp. 9").

Comp. 1-9, wherein the α-adrenergic antagonist is selected from the group consisting of doxazosin, prazosin, terazosin, phenoxybenzamine, phentolamine, tolazoline, trazodone, alfuzosin, tamsulosin, silodosin, atipamezole, idazoxan, mirtazapine, yohimbe, carvedilol, chlorpromazine, and/or labetalol (hereinafter: "Comp. 10").

Comp. 1-10, comprising between about 15 wt. % and about 75 wt. % of a carrier (hereinafter: "Comp. 11").

Comp. 1-11, wherein the carrier is selected from the group comprising lipids, phospholipids, alcohols, glycols, water, and/or solvents (hereinafter: "Comp. 12").

Comp. 1-12, wherein the carrier is petroleum jelly (hereinafter: "Comp. 13").

Comp. 1-13, further comprising a penetration enhancer, wherein the penetration enhancer comprises sulphoxides, azones, pyrrolidones, fatty acids, glycols, essential oils, terpenes, terpenoids, oxazolidinones, urea, nonionic surfactants, cationic surfactants, anionic surfactants, and/or zwitterionic surfactants (hereinafter: "Comp. 14").

Comp. 1-14, further comprising an anesthetic, wherein the anesthetic comprises lidocaine, morphine, barbiturates, benzodiazepines, etomidate, ketamine, propofol, dibucaine, dyclonine, prilocaine, articaine, bupivacaine, etidocaine, mepivacaine, chloroprocaine, procaine, tetracaine, and/or benzocaine (hereinafter: "Comp. 15").

Comp. 1-15, further comprising an additional vasodilator, wherein the additional vasodilator comprises prostaglandin, sildenafil citrate, sildenafil, tadalafil, bosentan, acetylcholine, benazepril, captopril, enalapril, fosinopril, lisinopril, moexipril, perindopril, quinapril, ramipril, trandolapril, azilsartan, candesartan, eprosartan, irbesartan, telmisartan, valsartan, losartan, olmesartan, amlodipine, clevidipine, diltiazem, felodipine, isradipine, nicardipine, nimodipine, nisoldipine, verapamil, isosorbide mononitrate, isosorbide dinitrate, hydralazine, minoxidil, fenoldopam, and/or nitroprusside (hereinafter: "Comp. 16").

Comp. 1-16, wherein the composition is provided as a lotion, cream, gel, stick, emollient, spray, topical ointment, oozing ointment, paste, powder, film-forming product, a solid composition, a liquid concentrate, a liquid dilution, as part of a patch, particularly an extended release patch, an instillation composition, wherein the composition is delivered to a target site by continuous and/or periodic instillation, as part of negative pressure therapy, and/or as part of a bandage/dressing (hereinafter: "Comp. 17").

Comp. 1-17, wherein the composition has a half-life of at least about 6 hours and provides a sterility assurance level (SAL) of at least $10^{-3}$ (hereinafter: "Comp. 18").

A method of administering a composition comprising: providing a composition for improving tissue perfusion comprising a phosphodiesterase inhibitor; a calcium channel blocker; a nitric oxide producer; an α-adrenergic antagonist; and
  a carrier; and
  applying the composition to a target skin or tissue surface;
    wherein the application provides a therapeutically effective amount of the composition at the target skin or tissue surface; and
  wherein the spray or foam improves tissue perfusion and inhibits the incidence of necrosis (hereinafter: "Method 1").

Method 1, further comprising the step of reapplying the composition during a desired time frame, wherein the desired time frame is between about once every 30 minutes to once a week, including once an hour, twice a day, three times a day, four times a day, five times a day, six times a day, every other day, twice a week, three times a week, once a week, twice a month, and/or once a month.

The inventions being thus described, it will be obvious that the same may be varied in many ways. Such variations are not to be regarded as a departure from the spirit and scope of the inventions and all such modifications are intended to be included within the scope of the following claims. The above specification provides a description of the manufacture and use of the disclosed compositions and methods. Since many embodiments can be made without departing from the spirit and scope of the invention, the invention resides in the claims.

What is claimed is:

1. A vasoactive composition for improving tissue perfusion comprising:
   from about 10 wt. % to about 30 wt. % of a phosphodiesterase inhibitor;
   from about 5 wt. % to about 35 wt. % of a calcium channel blocker, wherein the calcium channel blocker is magnesium sulfate;
   from about 0.1 wt. % to about 30 wt. % of a nitric oxide producer;
   from about 0.1 wt. % to about 30 wt. % of an α-adrenergic antagonist; and
   from about 15 wt. % to about 75 wt. % of a carrier.

2. The composition of claim 1, comprising between about 10 wt % and about 20 wt % of the phosphodiesterase inhibitor.

3. The composition of claim 2, wherein the phosphodiesterase inhibitor is selected from the group consisting of vinpocetine, erythron-9-(2-hydroxy-3-nonyl) adenine, (2-[(3,4-dimethoxyphenyl)methyl]-7-[(1R)-1-hydroxyethyl]-4-phenylbutyl]-5-methyl-imidazo[5,1-f][1,2,4]triazin-4 (1H)-one), oxindole, (9-(6-Phenyl-2-oxohex-3-yl)-2-(3,4-dimethoxybenzyl)-purin-6-one), inamrinone, amrinone, anagrelide, cliostazol, mesembrenone, rolipram, ibudilast, piclamilast, luteolin, drotaverine, roflumilast, apremilast, crisaborole, sildenafil, dipyridamole, quinazoline, papaverine, caffeine, aminophylline, 2-isobutyl-1-methylxanthine, paraxanthine, pentoxifylline, lisofylline, propentofylline, cliostazol, theobromine, and/or theophylline.

4. The composition of claim 1, comprising between about 1 mEq to about 50 mEq of a calcium channel blocker.

5. The composition of claim 4, wherein the calcium channel blocker is selected from the group consisting of nifedipine, clevidipine, nitrendipine, nicardipine, lercarnidipine, amlodipine, bepridil, felodipine, nisoldipine, diltiazem, verapamil, gallopamil, and/or magnesium sulfate.

6. The composition of claim 1, comprising between 5 wt % to 25 wt % of the nitric oxide producer.

7. The composition of claim 6, wherein the nitric oxide producer is selected from the group consisting of nitrate compounds, nitrite compounds, nitroso compounds, organic nitrates and/or nitrates, N-diazeniumdiolates, and/or S-nitrosothiols.

8. The composition of claim 7, wherein the organic nitrates and/or nitrates are selected from the group consisting of nitroglycerin, isosorbide dinitrate, isosorbide mononitrate, isoamyl nitrite, and combinations thereof.

9. The composition of claim 1, comprising between about 5 wt % and 25 wt % of the α-adrenergic antagonist.

10. The composition of claim 9, wherein the α-adrenergic antagonist is selected from the group consisting of doxazosin, prazosin, terazosin, phenoxybenzamine, phentolamine, tolazoline, trazodone, alfuzosin, tamsulosin, silodosin, atipamezole, idazoxan, mirtazapine, yohimbe, carvedilol, chlorpromazine, and/or labetalol.

11. The composition of claim 1, comprising between about 25 wt % and 20 wt % of the carrier.

12. The composition of claim 11, wherein the carrier is selected from the group consisting of: lipids, phospholipids, alcohols, glycols, water, solvents, and combinations thereof.

13. The composition of claim 12, wherein the carrier is petroleum jelly.

14. The composition of claim 1, further comprising a penetration enhancer, wherein the penetration enhancer is selected from the group consisting of sulphoxides, azones, pyrrolidones, fatty acids, glycols, essential oils, terpenes, terpenoids, oxazolidinones, urea, nonionic surfactants, cationic surfactants, anionic surfactants, zwitterionic surfactants, and combinations thereof.

15. The composition of claim 1, further comprising an anesthetic, wherein the anesthetic is selected from the group consisting of lidocaine, morphine, barbiturates, benzodiazepines, etomidate, ketamine, propofol, dibucaine, dyclonine, prilocaine, articaine, bupivacaine, etidocaine, mepivacaine, chloroprocaine, procaine, tetracaine, benzocaine, and combinations thereof.

16. The composition of claim 1, further comprising an additional vasodilator, wherein the additional vasodilator is selected from the group consisting of prostaglandin, sildenafil citrate, sildenafil, tadalafil, bosentan, acetylcholine, benazepril, captopril, enalapril, fosinopril, lisinopril, moexipril, perindopril, quinapril, ramipril, trandolapril, azilsartan, candesartan, eprosartan, irbesartan, telmisartan, valsartan, losartan, olmesartan, amlodipine, clevidipine, diltiazem, felodipine, isradipine, nicardipine, nimodipine, nisoldipine, verapamil, isosorbide mononitrate, isosorbide dinitrate, hydralazine, minoxidil, fenoldopam, nitroprusside and combinations thereof.

17. The vasoactive composition of claim 1, wherein the composition is in the form of a lotion, cream, gel, stick, emollient, spray, topical ointment, liquid ointment, paste, powder, film-forming product, a solid composition, a liquid concentrate, a liquid dilution, or an instillation composition.

18. A method of improving perfusion in a tissue in need thereof in a subject, the method comprising administering to the tissue an effective amount of the vasoactive composition of claim 1.

19. The method of claim 18, wherein the vasoactive composition is in the form of a spray or foam.

20. The method of claim 18, wherein the vasoactive composition is administered topically.

* * * * *